United States Patent [19]

Pawloski

[11] 4,087,430

[45] May 2, 1978

[54] PYRIDYL-PHOSPHONAMIDOTHIOATES, PYRIDYLPHOSPHORODIAMIDOTHIO-ATES, OXY ANALOGUES THEREOF AND DERIVATIVES THEREOF

[75] Inventor: Chester E. Pawloski, Bay City, Mich.

[73] Assignee: The Dow Chemical Company, Midland, Mich.

[21] Appl. No.: 758,217

[22] Filed: Jan. 10, 1977

Related U.S. Application Data

[63] Continuation-in-part of Ser. No. 619,862, Oct. 6, 1975, abandoned, which is a continuation of Ser. No. 468,846, May 10, 1974, abandoned.

[51] Int. Cl.$^2$ .................... C07D 213/02; A01N 9/22
[52] U.S. Cl. .................... 260/294.8 K; 260/296 R; 424/200
[58] Field of Search .................... 260/294.8 K, 296 R; 424/200

[56] References Cited

U.S. PATENT DOCUMENTS 3,911,118  10/1975  O'Melia .................... 424/200

*Primary Examiner*—Alan L. Rotman
*Attorney, Agent, or Firm*—Edward E. Schilling

[57] ABSTRACT

Substituted pyridinyl phosphonamidates, phosphonamidothioates, phosphorodiamidates and phosphorodiamidothioates which are useful in the control of nematodes.

11 Claims, No Drawings

PYRIDYL-PHOSPHONAMIDOTHIOATES, PYRIDYLPHOSPHORODIAMIDOTHIOATES, OXY ANALOGUES THEREOF AND DERIVATIVES THEREOF

CROSS-REFERENCE TO RELATED APPLICATIONS

The present application is a continuation-in-part of my copending application Ser. No. 619,862, filed October 6, 1975, now abandoned which is, in turn, a continuation of earlier filed application, Ser. No. 468,846, filed May 10, 1974 and now abandoned.

BACKGROUND OF THE INVENTION

1. Field of the Invention

The invention relates to novel substituted pyridinyl phosphonamidates, phosphonamidothioates, phosphorodiamidates and phosphorodiamidothioates and to their use in the control of soil nematodes.

2. Description of the Prior Art

Demosay et al. in U.S. Pat. No. 3,669,975, teach pesticidal activity, including nematicidal activity, for certain 6-methyl-3-pyridyl phosphates and thiophosphates having as an essential feature of the molecule RO substituent on the phosphorus atom. There is no exemplification of nematicidal activity in the patent disclosure and compounds such as O,O-diethyl O-(6-methyl-3-pyridinyl) thiophosphate have been found to have little or no nematicidal activity at reasonable field application rates. Moveover, while O-(6-methyl-3-pyridinyl) N-methyl ethylphosphoramidothioate has been found to exhibit some nematicidal activity, O-(6-methyl-3-pyridinyl) N-methyl ethylphosphonamidothioate is not similarly active. The nematicidal activity of these compounds is clearly not as predictable as might be deduced on reading Demosay et al.

Rigterink, in U.S. Pat. No. 3,743,648, discloses and claims pesticidal pyridinyl phosphates and phosphorothioates having, as an essential feature, a trifluoromethyl group on the pyridinyl ring. While the broad teachings are not so limited, each of the examples of Rigterink show a 2-pyridinyl or 4-pyridinyl compound. Furthermore, in those compounds of Rigterink in which notable nematicidal activity was found, the $CF_3$ group is at the 4-position and the ester-oxygen linkage is at the 2-position of the pyridinyl ring.

SUMMARY OF THE INVENTION

The present invention relates to certain novel substituted pyridinyl phosphonamidates, phosphonamidothioates, phosphorodiamidothioates and phosphorodiamidates of the following formula:

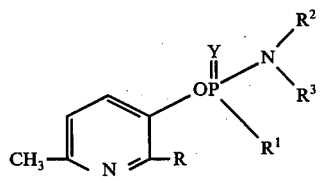
(I)

wherein Y represents a chalcogen of atomic number 8 to 16, inclusive, R represents hydrogen or lower alkoxy; $R^1$ represents -NHmethyl, -NHethyl, or methyl; $R^2$ represents hydrogen and $R^3$ represents methyl or ethyl.

The compounds of the above formula, hereinafter referred to for convenience as "active ingredients", are useful for the control of soil nematodes.

DETAILED DESCRIPTION OF THE INVENTION

The active ingredients of the present invention are usually oily liquids or solids at ambient temperatures and are soluble in usual organic carriers such as, for example, carbon tetrachloride, acetone, toluene, methylene chloride, dimethylformamide and the like.

The term "loweralkoxy" as used herein means methoxy, ethoxy, propoxy, isopropoxy and the like. The term "chalcogen" as employed in the present specification and claims means those members of the recognized chalcogen group having an atomic number of 8 to 16, inclusive, i.e., oxygen and sulfur.

The active ingredients of the above Formula I wherein Y is sulfur constitute a preferred embodiment of the present invention. Another preferred class of compounds includes those wherein R is hydrogen. An additional preferred embodiment includes active ingredients wherein R is alkoxy. A further preferred embodiment includes active ingredients wherein Y is sulfur, $R^1$ is -NHmethyl, R and $R^2$ are each hydrogen and $R^3$ is methyl. In another preferred embodiment, Y is sulfur, $R^1$ is -NHethyl, R and $R^2$ are each hydrogen and $R^3$ is ethyl. In still another preferred embodiment, Y is sulfur, R is alkoxy, $R^1$ and $R^3$ are each methyl and $R^2$ is hydrogen. A preferred compound of the present invention is O-(6-methyl-3-pyridinyl) N,N'-dimethylphosphorodiamidothioate.

The active ingredients of the present invention are prepared by reacting a selected substituted 3-pyridinol reactant with phosphorochloridate or phosphorochloridothioate and treating the thus formed intermediate with an amine reactant to form the desired substituted pyridinyl phosphorodiamidate or phosphorodiamidothioate. The substituted pyridinyl phosphonamidates and phosphonamidothioates are similarly prepared by employing methyl or ethyl substituted phosphonoic-or phosphonothioic-chloride starting materials. The reaction is usually carried out in the presence of an inert organic carrier medium, such as, for example, benzene, toluene, xylene, acetone, methyl isopropylketone, methyl isobutylketone, acetonitrile, dimethylformamide, methylene chloride and the like.

In carrying out the reaction, the pyridinol reactant is mixed with the carrier medium and an alkaline earth or alkali metal source, e.g., sodium hydroxide, potassium carbonate and the like, to form the salt of the pyridinol reactant. The mixture is then cooled to temperatures of from about 5° to about −10° C. and the phosphorochloridate, phosphorochloridothioate, phosphonochloridate or phosphonochloridothioate reactant added thereto. Generally, equimolar amount of reactants are employed. The resulting reaction mixture is stirred for a period of from about one-half to two hours and then cooled to below about 10° C. The amine reactant, e.g., methylamine or ethylamine, is slowly added to the cooled reaction mixture. Usually, depending upon the product desired and reactants employed, a two-to-four-fold equimolar amount of the amine reactant is employed. Following the completion of the amine addition, the reaction mixture is stirred for a period of from about 1 to about 5 hours at temperatures ranging from about 0° to about 25° C. The reaction mixture is then mixed with ice water and the mixture stirred for a period of from about 15 to about 30 minutes. The organic product layer is then separated, washed, dried over sodium sulfate and filtered. The product layer is distilled to remove the organic carrier and the product recovered as an oil or as a crystalline solid.

The following example illustrate the present invention but are not to be construed as limitations upon the same.

EXAMPLE 1

3-Hydroxy-6-methylpyridine (16.4 grams; 0.15 mole) and 50% sodium hydroxide (12.0 grams; 0.15 mole) were mixed with 300 milliliters (ml.) of methyl isobutylketone and the resulting mixture stirred and heated at reflux temperatures to distill off any water present. The mixture was then cooled to about $-6°$ C. in a salt water ice bath and $PSCl_3$ (25.5 grams; 0.15 mole) was added thereto. An exotherm to about 8° C. resulted. The mixture was stirred for about 90 minutes at a temperature of about $-4°$ C. and methylamine (18.6 grams; 0.60 mole) was then bubbled into the reaction mixture over a period of about one hour. The mixture was then stirred for about 2 hours in an ice bath then allowed to stand for about 15 hours. About 200 ml. of ice water were then added to the reaction mixture and the mixture was stirred for about 30 minutes. The organic product layer was separated from the aqueous layer and further washed with about three 125 ml. portions of water. The product layer was then treated with 200 ml. of a 2% sodium hydroxide solution for a period of about 15 minutes and the product layer again separated from the aqueous layer and washed with three additional 100 ml. portions of water. Following the separation of the organic product layer from the aqueous portion of the mixture, the product layer was dried over sodium sulfate, filtered and distilled at a temperature of 100° C. at 0.4 millimeters of mercury. The amber liquid thus obtained yielded a crystalline precipitate on standing. As a result of such operations, the desired O-(6-methyl-3-pyridinyl) N,N'-dimethylphosphorodiamidothioate product was obtained as a crystalline solid melting at 58°–63° C.

EXAMPLE 2

6-Methyl-3-pyridinol (11.0 grams; 0.1 mole) and methylphosphonothioic dichloride (15.0 grams) were mixed with 250 ml. of methylene chloride and the resulting reaction mixture was stirred and cooled in an ice bath. Triethylamine (11.0 grams) was added dropwise to the reaction mixture at a rate calculated to maintain the reaction mixture temperature below about 5° C. After this addition, the reaction mixture was stirred for two hours while warming to ambient room temperature. The reaction mixture was again cooled in an ice-water bath while methylamine (6 grams; 0.2 mole) was bubbled into the reaction mixture. Following the completion of the methylamine addition, the reaction mixture was stirred for a period of about four hours at ambient temperatures. After this period, 200 ml. of ice water were added to the reaction mixture, which was then stirred for a period of about 15 minutes. The organic product layer was then separated from the aqueous mixture and stirred with 200 ml. of a 2% sodium hydroxide solution for about 15 minutes. The organic product layer was again separated, washed with two 200 ml. portions of water, again separated and dried over sodium sulfate. The organic product layer was then filtered and distilled under reduced pressure until substantially all of the methylene chloride was removed. As a result of such operations, the desired O-(6-methyl-3-pyridinyl) N-methyl methylphosphonamidothioate was obtained as an oil having a refractive index $n_D^{25°}$ C. $= 1.5704$.

Other active ingredients of the present invention are similarly prepared according to the teachings of the specification and the foregoing examples by employing the appropriate substituted pyridinol and substituted phosphoro-chloridate or chloridothioate or phosphonic- or phosphonothioicchloride reactants. Such other products include, inter alia, the following:

O-(6-methyl-2-propoxy-3-pyridinyl) N,N'-dimethylphosphorodiaminothioate, having a refractive index $n_D^{25°}$ C. $= 1.5442$;

O-(6-methyl-3-pyridinyl) N,N'-dimethylphosphorodiamidate;

O-(2-methoxy-6-methyl-3-pyridinyl) N-methyl-N'-ethylphosphorodiamidothioate;

O-(6-methyl-3-pyridinyl) N-methyl methylphosphonamidate; and

O-(6-methyl-3-pyridinyl) N-methyl methylphosphonamidothioate.

The active ingredients of the present invention are useful in the control of soil nematodes. In the context of this disclosure, the term "nematicide" is employed to designate a compound that kills, inactivates, repels or otherwise prevents the destructive effects of nematodes, i.e., those members of the phylum Nemata, such as, for example, root knot nematodes (*Meloidogyne incognita var. acrita*), sugar beet cyst nematodes (*Heterodera schachtii*), and the like.

In use, the active ingredients are applied to areas to be protected from nematodes in any of a variety of formulations and means of application. In applying the active ingredients for nematode control, the active ingredient is of course applied in an amount sufficient to exert the desired control. The required amount, however, will be governed by such variables as method of applications, area of application, time of year, temperatures, moisture, and the like. The active ingredients of the present invention can be applied to areas to be protected from nematodes prior to crop planting. Many of the active ingredients of the present invention are safe to growing plants at well above the necessary use rates and can therefore be used during crop planting and also in certain standing crops.

Compositions of this invention suitable for practical use as nematicides will include one or more active ingredients of Formula I above either individually, in admixture with one another, or in admixture with other pesticides, and can include surface-active agents and inert carriers such as solid or liquid diluents and other inert materials as described to produce wettable powders, suspensions, emulsifiable concentrates, dusts, solutions, granules, petters or high-strength compositions.

In general, good nematicidal results are obtained when the active ingredients of the present invention are distributed through the soil in amounts of from about 0.1 to 1000 parts or more by weight per million parts by weight of soil. In field applications, the active ingredients may be distributed in the soil at a dosage of at least about one-half pound per acre foot of soil and through a cross-section of the soil as to provide for the presence therein of a nematicidal concentration of active ingredient. In such applications, it is desirable that the active ingredient be distributed to a depth of at least 12 inches below the soil surface.

The exact concentration of an active ingredient of Formula I to be employed in compositions for the treatment of growth media may vary provided nematicidal dosages of the active ingredients are supplied. The concentration of active ingredients in liquid compositions employed to supply the desired dosage generally is from about 0.01 to 50 percent by weight although as high a concentration as 90 percent by weight may be employed. In dusts, the effective weight may be from about 1 to 20 percent by weight. In compositions to be employed as concentrates, the active ingredients may be present in a concentration of from about 5 to 95 percent by weight.

Liquid compositions containing the desired amount of active ingredient may be prepared by dispersing the same in an inert diluent such as water or an organic liquid with the aid of a suitable surface-active dispersing agent such as an ionic or non-ionic emulsifying agent. The surface-active dispersing agents are generally employed in the amount of from 1 to 20 percent by weight of the combined weight of the active ingredient and surface-active agent in the composition. Suitable organic liquid carriers include acetone, xylene, toluene, isopropanol, polyglycols, chlorinated hydrocarbons such as methylene chloride, carbon tetrachloride, chlorobenzene and the petroleum distillates such as diesel fuel, kerosene, fuel oil, naphthas, and Stoddard solvent. Among the latter, the petroleum distillates boiling almost entirely under 400° F. at atmospheric pressure and having a flash point above 80° F. are generally preferred, however, any suitable liquid carrier or combination of carriers can be employed. The aqueous compositions may contain a small amount of a water-immiscible solvent whereby the carrier comprises an aqueous emulsion, namely, a mixture of water, emulsifying agent and organic liquid. In the liquid compositions, the choice of dispersing and emulsifying agent and the amount thereof employed are dictated by the nature of the composition and by the ability of the agent to facilitate the dispersion of the active ingredient in the carrier to produce the desired composition. Dispersing and emulsifying agents which may be employed in the compositions include the condensation products of alkylene oxides with phenols and organic acids, alkyl aryl sulfonates, polyoxyethylene derivatives of sorbitan esters, complex ether alcohols, mahogany soaps and the like.

In the preparation of dust compositions, the active ingredients are dispersed in and on finely divided inert solids such as clay, talc, chalk, gypsum and the like. In such operations, the finely divided carrier is mechanically mixed or ground with the active ingredient. Similarly, dust compositions containing the active ingredients may be prepared from various solid surface-active dispersing agents such as bentonite, fuller's earth, attapulgite and other clays. Depending upon the proportions of ingredients, these dust compositions may be employed as concentrates and subsequently diluted with additional solid surface-active dispersing agent or with chalk, talc, diatomaceous earth or gypsum and the like to obtain the desired amount of active ingredient in a composition adapted to be employed for the treatment of soil. Also, such dust compositions may be dispersed in water with or without the aid of a dispersing agent to form spray mixtures.

When operating in accordance with the present invention, the active ingredients of Formula I are dispersed in soil or growth media in any convenient fashion, e.g., by simply mixing with the soil, by applying to the surface of the soil and thereafter dragging or disking into the soil to be desired depth, by employing a liquid carrier to accomplish the penetration and impregnation or by injection or drilling techniques whereby the toxicant is deposited beneath the surface of the soil.

In a further method, the distribution of the active ingredients in soil or growth media may be accomplished by introducing the active ingredients in the water employed to irrigate the soil. The O-(6-methyl-3-pyridinyl) N,N'-dimethylphosphorodiamidothioate compound is especially effective when employed in this manner with sufficient irrigation water to translocate the compound to a soil depth of 12 or more inches. In such procedures, the amount of water may be varied with the porosity and water-holding capacity of the soil to obtain the desired depth of distribution of the active ingredients.

The following examples are illustrative of the use of the active ingredients of the present invention.

EXAMPLE 3

Separate acetone solutions containing 50 grams of one of the test ingredients: O-(6-methyl-3-pyridinyl) N,N'-dimethylphosphorodiamidothioate, O-(6-methyl-3-pyridinyl) N-methyl methylphosphonamidothioate and O-(6-methyl-2-propoxy-3-pyridinyl) N,N'-dimethylphosphorodiamidothioate, respectively, (hereinafter, Compounds A, B and C, respectively) per liter of solution were prepared for the treatment of separate seed beds (150 gram samples) containing sandy loam soil which was heavily infested with root knot nematodes (*Meloidogyne incognita var. acrite*). A portion of the soil samples was placed in a container and thereafter treated with the fumigant composition. In the treating operations, separate portions of each of the prepared compositions were injected into separate soil samples at various concentrations and the samples mixed to uniformly distribute the test chemical. The soil was then tamped and five cucumber seeds laid on the surface and the remaining treated soil portion added as a cap. Untreated soil samples were also planted with cucumber seeds to serve as checks. The soil samples were then maintained under conditions conducive to growth for a period of three weeks. At the end of this growth period, the plants were removed from the soil and the roots washed and examined for evidence of attack by nematodes. Examination of the plants indicated that Compound C gave complete control of nematodes at a concentration of 10.0 parts per million (ppm) by weight of soil while Compound B gave 75% control at application rates of 10.0 and 2.0 ppm, respectively. From an average of two replicates, Compound A was found to give 90, 90 and 50 percent control, respectively, of soil nematodes at application rates of 10.0, 2.0 and 0.4 ppm, respectively, by weight of soil.

EXAMPLE 4

An acetone solution of O-(6-methyl-3-pyridinyl) N,N'-dimethylphosphorodiamidothioate (Compound A) was prepared as in Example 3. Cylindrical plastic tubes, about 1-3/16 inch diameter and about 33-½ inch in length, were filled with nematode-infected soil to a height of about 24 inches. The test solutions containing various concentrations of the test ingredient were drenched onto the soil in the soil-filled tubes, which were supported in an upright position to insure proper drainage. In one set of operations (A), 100 milliliters (ml.), equivalent to about 5-acre inches of water, were applied at one time to certain of the soil-filled tubes. In another set of operations (B), 10 ml. of test solution (about one-half acre inch of water) were applied to soil-filled tubes and one-acre inch of water (20 ml.) added thereto on each of the five following days. All tubes, including untreated control tubes, were incubated for a period one week following the initial application of test solution in Operation A and following the last addition of water in Operation B. After such periods, the soil-filled tubes were laid horizontal, the top one-half of the longitudinal surface of each tube was removed, thereby exposing entire length of the soil column. The soil column was then cut into sequential three-inch increments (e.g., increments of 0–3, 3–6, 6–9 and the like) and the increments were placed into a pot and planted with cucumber seeds. Three weeks after planting, the cucumber plant roots were exposed, washed, and evaluated for nematode control. In operation A, the O-(6-methyl-3-pyridinyl) N,N'-dimethylphosphorodiamidothioate test ingredient was found to give from about 83 to 100% control of nematodes in all increment samples from the initial surface sample (0–3 inch) down through the 12–15 inch increment sample and 50% control of nematodes in the 15–18 inch increment at a dosage rate of 10 pounds per surface acre. At a dosage rate of 2.5 pounds per surface acre, the same test ingredient gave from 75 to 100 percent control of nematodes in all increments through the 15–18 inch increment.

In operation B, the test ingredient was found to give from 88 to 100% control of nematodes in all increment samples from the surface sample down through the 12–15 inch increment and 63% control in the 15–18 inch increment at a dosage rate of 10 pounds per acre. At a dosage rate of 2.5 pounds per acre, good control was achieved only through the 6–9 inch increment.

The foregoing data indicate the excellent soil movement and resulting high soil depth activity of the O-(6-methyl-3-pyridinyl) N,N'-dimethylphosphorodiamidothioate compound when applied with high initial amounts of irrigation water.

The other compounds of the invention when employed in substantially the same manner as used in Operations A and B give similarly excellent results in moving through the soil and controlling soil nematodes.

The reactants employed in preparing the active ingredients of the present invention are either readily available or can be readily prepared according to known procedures.

What is claimed is:

1. A compound of the formula:

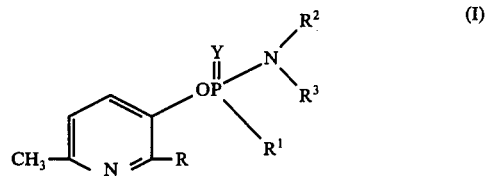

wherein Y represents a chalcogen of atomic number 8 to 16, inclusive; R represents hydrogen or lower alkoxy; $R^1$ represents -NHmethyl, -NHethyl or methyl; $R^2$ represents hydrogen and $R^3$ represents methyl or ethyl.

2. The compound of claim 1 wherein Y is a chalcogen of atomic number 16.

3. The compound of claim 1 wherein R is hydrogen.

4. The compound of claim 2 wherein R is hydrogen.

5. The compound of claim 1 wherein R is alkoxy.

6. The compound of claim 4 wherein $R^1$ is -NHmethyl and $R^3$ is methyl.

7. The compound of claim 5 wherein $R^1$ and $R^3$ are each methyl and $R^2$ is hydrogen.

8. The compound of claim 4 wherein $R^1$ and $R^3$ are each methyl and $R^2$ is hydrogen.

9. The compound of claim 6 which is O-(6-methyl-3-pyridinyl) N,N'-dimethylphosphorodiamidothioate.

10. The compound of claim 8 which is O-(6-methyl-3-pyridinyl) N-methyl methylphosphonamidothioate.

11. The compound of claim 7 which is O-(6-methyl-2-propoxy-3-pyridinyl) N,N'-dimethylphosphorodiamidothioate.

* * * * *